US012599620B2

(12) United States Patent
Fluge et al.

(10) Patent No.: US 12,599,620 B2
(45) Date of Patent: Apr. 14, 2026

---

(54) METHOD FOR THE TREATMENT OF CHRONIC FATIGUE SYNDROME USING AN INHIBITORY OR CYTOTOXIC AGENT AGAINST PLASMA CELLS

(71) Applicant: Vestlandets Innovasjonsselskap AS, Bergen (NO)

(72) Inventors: Øystein Fluge, Morvik (NO); Olav Mella, Olsvik (NO)

(73) Assignee: Vestlandets Innovasjonsselskap AS, Bergen (NO)

( * ) Notice: Subject to any disclaimer, the term of this patent is extended or adjusted under 35 U.S.C. 154(b) by 1076 days.

(21) Appl. No.: 17/638,453

(22) PCT Filed: Aug. 31, 2020

(86) PCT No.: PCT/EP2020/074186
§ 371 (c)(1),
(2) Date: Feb. 25, 2022

(87) PCT Pub. No.: WO2021/038097
PCT Pub. Date: Mar. 4, 2021

(65) Prior Publication Data
US 2022/0339174 A1 Oct. 27, 2022

Related U.S. Application Data

(60) Provisional application No. 62/893,838, filed on Aug. 30, 2019.

(51) Int. Cl.
| | |
|---|---|
| *A61P 25/00* | (2006.01) |
| *A61K 31/407* | (2006.01) |
| *A61K 31/69* | (2006.01) |
| *A61K 38/06* | (2006.01) |
| *A61K 38/07* | (2006.01) |
| *A61K 39/00* | (2006.01) |
| *A61K 39/395* | (2006.01) |

(52) U.S. Cl.
CPC ........... *A61K 31/69* (2013.01); *A61K 31/407* (2013.01); *A61K 38/06* (2013.01); *A61K 38/07* (2013.01); *A61K 39/3955* (2013.01); *A61P 25/00* (2018.01); *A61K 2039/507* (2013.01); *A61K 2039/545* (2013.01)

(58) Field of Classification Search
CPC ...... A61K 31/69; A61K 31/407; A61K 38/06; A61K 38/07; A61K 39/3955; A61K 2039/507; A61K 2039/545; A61K 2039/505; A61K 9/0019; A61K 31/675; A61K 38/05; A61K 45/06; A61K 40/4222; A61P 25/00; C07K 16/2887; G01N 2800/306
See application file for complete search history.

(56) References Cited

U.S. PATENT DOCUMENTS

| | | | |
|---|---|---|---|
| 3,773,919 | A | 11/1973 | Boswell |
| 5,736,137 | A | 4/1998 | Anderson et al. |
| 6,267,958 | B1 | 7/2001 | Andya et al. |
| 6,713,054 | B1 | 3/2004 | Ridihalgh |
| 2002/0136719 | A1 | 9/2002 | Shenoy |
| 2011/0142836 | A1 | 6/2011 | Mella et al. |
| 2017/0095473 | A1 | 4/2017 | Molineaux et al. |

FOREIGN PATENT DOCUMENTS

| | | |
|---|---|---|
| WO | 9856418 A1 | 12/1998 |
| WO | 2004/009776 A2 | 1/2004 |
| WO | 2009083602 A1 | 7/2009 |
| WO | 2016/102530 A1 | 6/2016 |
| WO | 2017/014788 A1 | 1/2017 |
| WO | 2017062354 A1 | 4/2017 |

OTHER PUBLICATIONS

Woodle ES, et al. Plasma cell targeting to prevent antibody-mediated rejection. Am J Transplant. (Year: 2020).*
Noor, N, et al. A comprehensive update of the current understanding of chronic fatigue syndrome. Anesthesiology and pain medicine (Year: 2021).*
Van de Donk, N WCJ. Immunomodulatory effects of CD38-targeting antibodies. Immunology letters (Year: 2018).*
Rivell GL, et al. Effectiveness and safety of high-dose cyclophosphamide as salvage therapy for high-risk multiple myeloma and plasma cell leukemia refractory to new biological agents. Am J Hematol (Year: 2011).*
Albright, F. et al., "Evidence for a heritable predisposition to Chronic Fatigue Syndrome", BMC Neurology 2011, 11:62.
Brenu, E. et a., "Longitudinal investigation of natural killer cells and cytokines in chronic fatigue syndrome/myalgic encephalomyelitis", Journal of Translational Medicine 2012, 10:88.
Carruthers, B. et al., "Myalgic Encephalomyelitis/Chronic Fatigue Syndrome: Clinical Working Case Definition, Diagnostic and Treatment Protocols".
Alexander, T. et al., "Proteasome inhibition with bortezomib induces a therapeutically relevant depletion of plasma cells in SLE but does not target their precursors", Eur. J. Immunol. 2018. 48: 1573-1579.

(Continued)

*Primary Examiner* — Gary B Nickol
(74) *Attorney, Agent, or Firm* — WCF IP

(57) ABSTRACT

The present disclosure relates in a first aspect to a method for the treatment of chronic fatigue syndrome (CFS) comprising administering to a patient in need thereof a therapeutically effective amount of inhibitory or cytotoxic agent against plasma cells. In a further aspect, the present disclosure relates to a combination of the inhibitory or cytotoxic agent against plasma cells with a B-cell depleting agent or an inhibitor of B-cell activation in the treatment of chronic fatigue syndrome. In addition, a combination of an inhibitory or cytotoxic agent against plasma cells and B-Cell depleting agent or an inhibitor of B-cell activation are described. Said combination may be provided in form of a kit comprising suitably effective dosages of said compounds. Further, the use of the compounds or the combination in the treatment of CFS is described.

3 Claims, No Drawings

(56)         References Cited

OTHER PUBLICATIONS

Chang, C. et al., "Chronic Fatigue Syndrome and Subsequent Risk of Cancer , Among Elderly US Adults", Cancer 2012.

Clark, E. et al., "Role of the Bp35 cell surface polypeptide in human B-cell activation", Proc. Nadl. Acad. Sci. USA vol. 82, pp. 1766-1770, Mar. 1985.

Øystein Fluge and Olav Mella, "Clinical impact of B-cell depletion with the anti-CD20 antibody rituximab in chronic fatigue syndrome: a preliminary case series", BMC Neurology 2009, 9:28.

Fluge, Ø. et al., "Benefit from B-Lymphocyte Depletion Using the Anti-CD20 Antibody Rituximab in Chronic Fatigue Syndrome. A Double-Blind and Placebo-Controlled Study", PLoS One 6:10, 2011.

Fluge, Ø. et al., "Metabolic profiling indicates impaired pyruvate dehydrogenase function in myalgic encephalopathy/chronic fatigue syndrome", JCI Insight. 2016;1(21):e89376.

Kaushik, N., "Gene expression in peripheral blood mononuclear cells from patients with chronic fatigue syndrome", J Clin Pathol 2005;58:826-832.

Keddie, S. et al., "Plasma cell depletion with bortezomib in the treatment of refractory N-methyl-D-aspartate (NMDA) receptor antibody encephalitis. Rational developments in neuroimmunological treatment", European Journal of Neurology 2018, 25: 1384-1388.

Khodadadi, L. et al., "Bortezomib Plus Continuous B Cell Depletion Results in Sustained Plasma Cell Depletion and Amelioration of Lupus Nephritis in NZB/WF1 Mice", PLOS ONE | DOI:10.1371/journal.pone.0135081 Aug. 7, 2015.

Mihaylova, I. et al., "Decreased expression of CD69 in chronic fatigue syndrome in relation to inflammatory markers: evidence for a severe disorder in the early activation of T lymphocytes and natural killer cells", Neuroendocrinology Letters vol. 28 No. 4 2007.

Nacul, L. et al., "Prevalence of myalgic encephalomyelitis/chronic fatigue syndrome (ME/CFS) in three regions of England: a repeated cross-sectional study in primary care", Nacul et al. BMC Medicine 2011, 9:91.

Ogawa, M. et al., "Decreased nitric oxide-mediated natural killer cell activation in chronic fatigue syndrome", European Journal of Clinical Investigation (1998) 28, 937-943.

Rekeland, I. et al., "Intravenous Cyclophosphamide in Myalgic Encephalomyelitis/Chronic Fatigue Syndrome. An Open-Label Phase II Study", Frontiers in Medicine | www.frontiersin.org Apr. 1, 2020 | vol. 7 | Article 162.

Scheibenbogen C, Loebel M, Freitag H, Krueger A, Bauer S, Antelmann M, et al. (2018) Immunoadsorption to remove û2 adrenergic receptor antibodies in Chronic Fatigue Syndrome CFS/ME. PLoS ONE 13(3): e0193672. https://doi.org/10.1371/journal.pone.0193672.

Staines, D. "Do vasoactive neuropeptides and heat shock proteins mediate fatigue-related autoimmune disorders?", Medical Hypotheses (2005) 64, 539-542.

Vollmer-Conna, U. et al., "Postinfective Fatigue Syndrome Is Not Associated with Altered Cytokine Production", Clinical Infectious Diseases, vol. 45, No. 6 (Sep. 15, 2007), pp. 732-735.

* cited by examiner

METHOD FOR THE TREATMENT OF CHRONIC FATIGUE SYNDROME USING AN INHIBITORY OR CYTOTOXIC AGENT AGAINST PLASMA CELLS

The present invention relates in a first aspect to a method for the treatment of chronic fatigue syndrome (CFS) comprising administering to a patient in need thereof a therapeutically effective amount of inhibitory or cytotoxic agent against plasma cells. In a further aspect, the present invention relates to a combination of the inhibitory or cytotoxic agent against plasma cells with a B-cell depleting agent or an inhibitor of B-cell activation in the treatment of chronic fatigue syndrome. In addition, a combination of an inhibitory or cytotoxic agent against plasma cells and B-Cell depleting agent or an inhibitor of B-cell activation are described. Said combination may be provided in form of a kit comprising suitably effective dosages of said compounds. Further, the use of the compounds or the combination in the treatment of CFS is described.

TECHNICAL BACKGROUND

Chronic fatigue syndrome (CFS) also described as myalgic encyophalitis (ME) is a disease affecting approximately 0.2 percent of the population (Nacul et al, BMC med 2011, 9:91). It is a disease affecting women three to four times more often than men and often preceded by an infection. It is speculated on a genetic predisposition for CFS (Albright et al, 2011, BMC neurol 11:62). According to the clinical working case definition (Canadian criteria) for CFS/ME, Carruthers B. M., et al., 2003, J. Chronic Fatigue Syndr, 11:7-36, the main symptoms are post-exertional malaise, with cognitive disturbances, pain, sensory hypersensitivity, and several symptoms related to neuroendocrine and autonomic function. CFS is characterized by an unexplained, severe fatigue, persisting for at least six consecutive months, and with a substantial reduction of previous levels in occupational, social or personal activities. Although many studies have been shown subtle alterations in blood tests or radiological investigations, no biomarker or diagnostic test exist.

That is, the aetiology of CFS remains unclear. Various hypotheses include immunological, virological, neuroendocrinological, and psychological mechanisms. The pathogenesis of CFS is presumed to be multifactorial and to involve both host and environmental factors.

Many patients suffering from CFS have a history of an acute viral infection preceding the development of fatigue. However, no persisting viral infection has been proven yet.

Furthermore, several gene expression studies have been performed in CFS, indicating that there are specific but complex gene alterations in accordance with the dysfunction in immune response and in defence mechanisms. For example, Kaushik N., et al., 2005, J. Clin Pathol 58:826-32 describe a microarray study showing differential expression of 16 genes in CFS suggesting T-cell activation and a disturbance of neuronal and mitochondrial function. Other microarray studies concluded that several genes affected mitochondrial function and cell cycle deregulation. Moreover, alterations in membrane transport and ion channels were described. Based on the numerous studies, the gene expression data are not conclusive but suggest that there are disturbances in CFS representing various cellular functions.

A study in 2007 of post-infective fatigue syndrome found no differences in ex vivo cytokine production over a 12-month period, as compared to controls recovering promptly after infection (Vollmer-Conna U., et al., 2007, Clin Infect Dis 45:732-5). It is speculated that CFS patients may have a reduced immune cell function with a low NK cell cytotoxicity and immunoglobulin deficiencies.

For example, Ogava M., et al., 1998, Eur J of Clin Invest, 28:937-943 describes decreased nitric oxide mediated natural killer cell activation in chronic fatigue syndrome. Namely, NO donor compounds were able to stimulate NK cell activity in healthy control subjects but not in NK cells obtained from CFS patients and stimulated in vitro.

Studies demonstrated several abnormalities in laboratory markers associated with immune functions in CFS patients. For example, a low NK cell cytotoxicity, but also an increase in CD8+ T cells, elevated numbers of CD20+ B-cells, and an increase in the B-cell subset expressing CD20 and CD5 has been described. A study comparing CFS patients and controls, reported decreased expression of CD69 on T cells in NK cells after mitogenic stimulation in vitro, indicating a disorder in the early activation of cellular immunity mediated by the cells (Mihaylova I., et al., 2007, Neuro Endocrinol Lett 28:477-83).

However, the data on immune bioregulation in CFS are not consistent, e.g. as discussed in Brenu et al, 2012, J Trans Med 10:88.

Along with hypotheses of immune deregulation in CFS, autoimmunity to endogenous vasoactive neuropeptides has been proposed as a mechanism for the disease, Staines D R., 2005, Med Hypotheses 64:539-42, however not supported by scientific data. Other reports are discussing various autoantibodies in conjunction with CFS. However, no clear association was proved. Thus, there is no direct evidence with consistent data for the presence of pathogenic autoantibodies or for T-lymphocyte mediated autoimmunity. That is, CFS is at present not defined as an autoimmune disease. Rather, CFS is still identified as a disease with unknown aetiology.

Various hypotheses for CFS pathogenesis are discussed in the art including blood platelet dysfunction, neurological, neuroendocrine, metabolic or autonomic disturbances, ion channel dysfunction, zinc deficiency, toxin exposure or prior vaccination, etc. However, no consistent picture has emerged for the aetiology and pathogenesis of CFS. Due to the lack of knowledge of the exact pathogenesis and with no known causal mechanism, there is no current standard specific treatment for CFS. The unknown aethiology of CFS is probably the reason for the remarkably few studies performed, evaluating therapy based upon a biological hypothesis.

Studies are described in the art testing treatment with immunoglobulins, or treatment with anti-viral compositions, like valganciclovir.

The inventors of the present invention published a series of case studies, Fluge O., Mella O., 2009, BMC Neurol. 9:28 followed by a double-blinded and placebo controlled, randomized phase II study, Fluge O., et al., 2011, PLOS 6:e26359, exploring B-cell depletion using the therapeutic monoclonal anti-CD20 antibody Rituximab, showing a clinical benefit in 2/3 of CFS patients. The use of B-cell depleting agents is described in WO 2009/083602. The patterns of responses and relapses, with a time delay of 2 to 8 eight months from start of Rituximab infusion (with rapid B-cell depletion) until start of clinical responses, indicate that an antibody may be involved in the pathogenesis. Recently, a case control study performed in elderly aged more than 65 years, investigating more than 1 million cases in cancer and 100,000 healthy controls, with a prevalence of CFS diagnosis of 0.5 percent in both groups, show that elderly CFS patients had a modest but highly significant risk of B-cell lymphomas, Chang C. M., Cancer, 2012, 118: 5929-36, consistent with a chronic B-cell activation. Taken together, the data on treatment with a monoclonal anti-CD20 antibody exemplified by Rituximab indicate that CFS in a subset of patients may be a post-infectious immune dysregulation, possibly a variant of autoimmune mechanisms, possibly with a genetic predisposition, in which B lymphocytes are important for symptom maintenance.

There is increasing evidence for underlying immune dysfunction in ME/CFS, including presence of autoantibodies in blood, and increased rates of B-cell lymphomas in elderly patients with a history of long-standing ME/CFS. Two clinical studies had been performed indicating that B-cell depletion with the CD20 directed therapeutic monoclonal antibody Rituximab could alleviate symptoms and increase function level in ME/CFS patients. Later a multicenter, randomized, double-blind and placebo-controlled study (RituxME) had been conducted, where the beneficial effect could not be verified, showing that Rituximab given according the study protocol is not a feasible treatment for patients with a clinical ME/CFS diagnosis based on only Canadian consensus criteria.

However, some ME/CFS patients treated in these studies have had a seemingly very good clinical response to Rituximab with major alleviation of the core symptoms. Upon recurrences, some patients have been retreated several times, often with the same pattern and time frame of responses.

However, as indicated above, using B-cell depletion by the monoclonal anti-CD20 antibody Rituximab in CFS, there is a significant delay from start of the treatment and the beginning of the symptoms relief. Also, in the initial clinical studies performed with Rituximab, approximately ⅔ of CFS patients had a clinical response. This is not only true for treatment with Rituximab, but can also be seen with treatment of methotrexate, a small molecule known as an active agent for B-cell depletion useful in the treatment of various kinds of diseases.

Thus, there is an ongoing need to provide additional compounds useful in the treatment of chronic fatigue syndrome. In particular, there is an ongoing need for providing compounds which act fast in the patients without the lag period described for the B-cell depleting agent. In addition, there is a continuous demand for compounds which may also be effective in patients not (initially) susceptible to B-cell depleting agent treatment.

Further patients with longstanding ME/CFS with significant symptomatic improvement when given Cyclophosphamide or Ifosfamide for an acquired cancer have been reported. Consequently, patients have been treated in a phase II trial with 6 courses of Cyclophosphamide and experienced significant clinical improvements of long duration in more than half the patients (Rekeland I G, et al., 2020, Front Med (Lausanne) 7: 162). Among immune cells, Cyclophosphamide has at our utilized trial doses an effect on both CD4+ and CD8+ T-cell subsets, and especially on T-regulatory cells. However, experience with the drug in autoimmune diseases show an effect of Cyclophosphamide on proliferating B-cells that halts the production of autoantibodies and reduces the formation of short-lived plasma cells, thus also the recruitment of mature plasma cells. A small clinical study with immune adsorption in ME/CFS can also support the presence of autoantibodies directed against adrenergic and muscarinic receptors (Scheibenbogen C, et al., 2018, PLoS One 13: e0193672).

CFS patients have a marked endothelial dysfunction assessed by FlowMediated Dilation (FMD), a test that (under standardized conditions) largely reflect Nitric Oxide (NO) synthesis in endothelial cells after shear stress. A markedly reduced FMD, transient clinical responses after long-acting nitrates (like isosorbide mononitrate) and the clinical picture of CFS, are the basis for a hypothesis according to the present invention in which a main mechanism for CFS symptom maintenance is a relative lack of endothelial-cell derived Nitric Oxide (NO) availability. This results in reduced NO diffusion from endothelial cells to surrounding cells such as smooth muscle cells in blood vessel walls, and with a resulting inadequate regulation of blood flow to meet the metabolic demands of tissues. Also a relative lack of endothelial-cell derived NO may result in cognitive disturbances, sleep problems, a low anaerobic threshold, and lactate accumulation in tissues after modest exertion, a low NK cell function, all reported to be associated with CFS.

Further, it has been demonstrated that plasma from patients with moderate and severe ME/CFS alters the energy metabolism of cultured muscle cells suggesting cellular stress, with some indications that the effect could be immunoglobulin-mediated (Fluge O, et al., 2016, JCI Insight 1: e89376).

In humans, different B-cells subpopulations can be distinguished in peripheral blood and other tissues on the basis of differential expression of various surface markers. From birth all the B-cells originate from common precursors in the bone marrow. In the bone marrow, peripheral blood and secondary lymphoid tissues, different B-cell populations can be distinguished, corresponding to different stages of maturation, activation and differentiation. B-cell development can be separated in an early antigen-independent phase, which takes place in the bone marrow and a late antigen-dependent phase, which takes place in the secondary lymphoid tissue. Generally, one can differentiate between the following B-cell lineage subsets, pro B-cells, pre B-cells, immature and transitional B-cells, mature naïve B-cells, memory B-cells, plasmablasts and plasma cells. Plasmablasts are recently differentiated antibody producing cells that are usually shortlived but can recirculate and home to tissues such as the precursor or the bone marrow, mature plasma cells are matured from plasmablasts and stay in the tissue where they produce large amount of antibodies.

As noted, the B-cells can be distinguished into major subpopulations by differential expression of various surface markers. E.g., CD20, a well known B-cell marker, is expressed on most of the B-cells beside terminally differentiated plasma cells and pro B-cells.

The principle of proteasome inhibition as treatment in some established autoantibody-mediated diseases refractory to other treatments, due to antibody production from mature plasma cells, has been demonstrated in small patient series. In patients with N-Methyl-D-Aspartate (NMDA) receptor antibody-mediated encephalitis refractory to other treatments (first and second line therapy with steroids, intravenous immunoglobulins, plasma exchange, Cyclophosphamide, Rituximab) Bortezomib intravenous infusions were followed by clinical improvement and reduction of pathologic autoantibodies (Keddie S, et al., 2018, Eur J Neurol 25: 1384-1388).

As recruitment of plasmablasts in patients with systemic lupus erythematosus (SLE) after bortezomib is rapid and thus allows autoantibody production to be resumed, the proteasome inhibitor treatment should be combined with a targeted therapy toward plasmablasts, specifically CD20 antibodies like Rituximab, given at time intervals short enough to attenuate plasma cell recruitment. Thus, the combined targeting of plasma cells and B-cells is emerging as a promising treatment principle in autoimmune diseases (Alexander T, et al., 2018, Eur J Immunol 48: 1573-1579). In animal models, Bortezomib plus B-cell depletion resulted in sustained plasma cell depletion and amelioration of lupus nephritis in mice (Khodadadi L, et al., 2015, PLoS One 10: e0135081).

An alternative approach for plasma cell depletion is to target the mature plasma cells directly, including memory cells, with antibodies directed toward epitopes on their surface. Such epitopes are not necessarily specific for plasma cells and must be used with care. A commercially available drug directed at CD38 (Daratumumab) is used for treatment of myeloma, because the myeloma cells typically have high densities of CD38 antigen. The drug will however also target other immune cells, such as activated T- and B-cells as well as myeloid-derived suppressor cells. The attenuation of this suppression may induce T-cell activity after the use of Daratumumab. Thus, even though targeting the plasma cells, Daratumumab may induce recruitment of other B-cells and therefore given alone may be not achieve the goal of effective and long-lasting suppression of long-lived plasma cells.

DESCRIPTION OF THE PRESENT INVENTION

In a first aspect, the present invention relates to a method for the treatment of chronic fatigue syndrome (CFS) comprising administering to a patient in need thereof a therapeutically effective amount inhibitory or cytotoxic agent against plasma cells.

That is, the present inventors recognized that administration of inhibitory or cytotoxic agent against plasma cells, relieve the symptoms of CFS and, thus, may be useful in the treatment of CFS, accordingly.

In particular, the present inventors recognized that an immediate or a rapid relief, e.g. within a week or weeks, from start of administration of said inhibitory or cytotoxic agent against plasma cells, e.g. by carefully increasing the dose, can be observed. In contrast to medication such as Rituximab for a treatment of CFS, which is characterized by a remarkable lag time before clinical responses, as described, e.g. WO 2009/083602. Hence, the administration of inhibitory or cytotoxic agent against plasma cells e.g. surprisingly allows a treatment of CFS patients for early relief of symptoms without a long delay as described for e.g. a B-Cell depleting agent, like Rituximab. It has been recognized by the inventors that plasma cells are involved in the disease mechanisms or therapy of CFS patients.

In the context of the present invention, the terms "chronic fatigue syndrome", CFS, and "Myalgic Encephalitis", ME, are used synonymously.

As used herein, the term "inhibitory or cytotoxic agent against plasma cells" refers to compounds which influence, namely inhibit or induce cell death of plasma cells. In particular, the compounds decrease immunoglobulin release or immunoglobulin (antibody) production of said cells.

Also patients with longstanding ME/CFS were observed to have significant symptomatic improvement when given Cyclophosphamide or Ifosfamide for an acquired cancer. Also, 40 patients in a phase II trial were treated with 6 courses of Cyclophosphamide and experienced significant clinical improvements of long duration in more than half the patients, as described above. Among immune cells, Cyclophosphamide has at our utilized trial doses an effect on both CD4+ and CD8+ T-cell subsets, and especially on T-regulatory cells. However, experience with the drug in autoimmune diseases show an effect of cyclophosphamide on proliferating B-cells that possibly halts the production of autoantibodies and reduces the formation of short-lived plasma cells, thus also the recruitment of mature plasma cells.

A small clinical study with immune adsorption in ME/CFS can also support the presence of autoantibodies directed against adrenergic and muscarinic receptors. It has been demonstrated that plasma from patients with moderate and severe ME/CFS alters the energy metabolism of cultured muscle cells suggesting cellular stress, with some indications that the effect could be immunoglobulin-mediated. These data may indicate that autoantibodies are present in a subset of ME/CFS patients, despite the negative RituxME study. As known from established autoimmune diseases, autoantibodies can be produced by both late plasmablasts (with or without CD20 antigen on their surface membrane) or from mature plasma cells which lack CD20 expression, depending on the underlying disease and patient. If a major disease mechanism in ME/CFS is autoantibody interaction within the patients, in practice only patients with autoantibodies produced in CD20 positive "early" plasmablasts would be expected to experience symptom relief from Rituximab. However, giving sufficient doses of Rituximab over a prolonged period could eventually reduce the recruitment of mature plasma cells and thus achieve a symptomatic effect in some patients.

The total available data is compatible with a subset of ME patients having an autoantibody-maintained disease, but also that the treatment offered until now (i.e. the therapeutic anti-CD20 antibody Rituximab) has not been sufficient and effective in reducing the load of the pathological immunoglobulins. Patients responding to Rituximab may have autoantibody production from immature plasma cells (plasmablasts). For most ME/CFS patients with autoantibody-production from the mature plasma cells, not responding to Rituximab, a possible way to treat ME/CFS could thus be by using a regimen that targets mature plasma cells, either because of plasma cell vulnerability to a drug with a general mode of action, or to a molecular targeted therapy directed against specific epitopes on mature plasma cells. In addition, recruitment of new plasma cells from B-cells, with the ability for autoantibody production, must be attenuated.

Consequently, ME/CFS can be treated with drugs that induce apoptosis and reduce autoantibody production in plasma cells. Specifically, this may be achieved by a proteasome inhibitor like Bortezomib. The class of drugs denoted as proteasome inhibitors act by inhibiting the chymotrypsin activity of the proteasome, accumulating misfolded proteins particularly in cells with high levels of protein turnover and especially in immunoglobulin-producing plasma cells. In myeloma, this will eventually lead to apoptosis of the malignant plasma cells. Experimental data indicate that these drugs also are beneficial in autoimmune disease by depleting activated T- and B-cells and by inhibition of type I interferon production in monocytes and plasmacytoid dendritic cells. Because of toxicity (especially peripheral neuropathy), and also the influence on long-lived plasma cells responsible for normal antibodies such as vaccine-induced antibodies, the drugs should preferably be given in a few (1-4) courses over a limited period of time.

The principle of proteasome inhibition as treatment in some established autoantibody-mediated diseases refractory to other treatments, due to antibody production from mature plasma cells, has been demonstrated in small patient series afflicted with other autoimmune diseases. In patients with N-Methyl-D-Aspartate (NMDA) receptor antibody-mediated encephalitis refractory to other treatments (first and second line therapy with steroids, intravenous immuno-globulins, plasma exchange, cyclophosphamide, Rituximab) Bortezomib Intravenous infusions were followed by clinical improvement and reduction of pathologic autoantibodies.

As recruitment of plasmablasts in patients with systemic lupus erythematosus (SLE) after bortezomib is rapid and thus allows autoantibody production to be resumed, in an embodiment of the present invention, the proteasome inhibitor treatment is combined with a targeted therapy toward plasmablasts, specifically CD20 antibodies like Rituximab, given at time intervals short enough to attenuate plasma cell recruitment. Thus, the combined targeting of plasma cells and B-cells is emerging as a promising treatment principle in autoimmune diseases. In animal models, Bortezomib plus B-cell depletion resulted in sustained plasma cell depletion and amelioration of lupus nephritis in mice. A protocol for a planned clinical trial of bortezomib treatment in some established autoimmune diseases has been published.

An alternative approach for plasma cell depletion is to target the mature plasma cells directly, including memory cells, with antibodies directed toward epitopes on their surface. Such epitopes are not necessarily specific for plasma cells and must be used with care. A commercially available drug directed at CD38 (Daratumumab) is used for treatment of myeloma, because the myeloma cells typically have high densities of CD38 antigen. The drug will however also target other immune cells, such as activated T- and B-cells as well as myeloid-derived suppressor cells. The attenuation of this suppression may induce T-cell activity after the use of Daratumumab. Thus, even though targeting the plasma cells, Daratumumab may induce recruitment of other B-cells and therefore given alone may not achieve the goal of effective and long-lasting suppression of long-lived plasma cells. Therefore combining a CD38-directed antibody like Daratumumab with maintenance Rituximab or another CD20-directed antibody, is a therapeutic choice.

Also other monoclonal antibodies directed to relatively selective plasma cell antigens, like anti-CD319 (Elotuzumab) could be used in combination with the B-cell depleting agent, like an anti-CD20 monoclonal antibody.

In an embodiment of the present invention, the plasma cells are CD20 negative plasma cells, namely, terminally differentiated plasma cells.

An embodiment of the present invention, a combination of at least two inhibitory or cytotoxic agent against plasma cells may be provided.

The route of administration of inhibitory or cytotoxic agent against plasma cells depends on the formulation used. That is inhibitory or cytotoxic agents against plasma cells may be administered in form of capsules or other suitable forms, like tablets.

The schedule for proteasome inhibition would depend on the drug. For bortezomib, usually either iv or sc injections of days 1, 4, 8 and 11 in one cycle, with a new cycle after 3-4 weeks.

In addition, the inhibitory or cytotoxic agent against plasma cells may be in a form of a compound of immediate relief or in a form of a delayed or sustained thereof. Furthermore, if applicable, the inhibitory or cytotoxic agent against plasma cells may be provided in powder formed for oral use.

For example, inhibitory or cytotoxic agent against plasma cells is adapted for systemic administration, for example via the enteral or parenteral route. In another embodiment, the inhibitory or cytotoxic agent against plasma cells is adapted for mucosal or local administration.

Moreover, in another embodiment, the inhibitory or cytotoxic agent against plasma cells useful in the treatment of CFS is adapted for the administration to a subject in a single therapeutically effective doses or multiple of therapeutically effective doses thereof. The skilled person is well aware of the effective dose to be administered. Typically, the daily doses is similar to the daily doses administered in the treatment of other diseases treated with said inhibitory or cytotoxic agent against plasma cells.

Typically, the inhibitory or cytotoxic agent against plasma cells useful in the treatment of CFS is in a suitable pharmaceutical form, for example, in combination with a pharmaceutically acceptable diluent, excipient or carrier. The pharmaceutical composition may contain additional components including pharmaceutical additives, pH-stabilizer, etc.

That is, the present invention provides a pharmaceutical composition comprising the inhibitory or cytotoxic agent against plasma cells as defined herein and a pharmaceutically acceptable diluent, excipient or carrier useful in the treatment of CFS.

The doses and administration are similar to the doses and administration as described for the inhibitory or cytotoxic agent against plasma cells in connection with other diseases and disorders. For example, the doses and administration is initially 0.5 to 2 mg daily gradually increasing the same over the first days. For example, after five days the doses is between 0.5 mg and 5 mg. The doses may be increased by 0.5 mg or 1 mg at intervals to a daily dosage of 2 to 10 mg. The skilled artisan is well aware of suitable dosage. The daily dosage may be taken once daily or several times daily, e.g. two times daily or three times daily. That is, the initial daily dosage is in the range of 0.5 to 3 mg active ingredient administered once or three times daily while increasing the same over the treatment period. The typical maximum dosage is about 10 mg daily dosage, e.g. 2.5 mg three times a day.

In an embodiment, the treatment and use is in a form that in a first treatment regimen, the inhibitory or cytotoxic agent against plasma cells is administered, e.g. as described above by administering cycles, for example, the active agent is given in one to four courses or cycles over a predetermined period of time.

Thereafter, the B-cell depleting agent is administered. The B-cell depleting agent may be administered in courses or cycles as described above.

The skilled person is well aware of suitable courses and treatment regimens accordingly.

That is, the dosis and administration are similar to dosis and administration of the compounds described for other diseases, disorders or conditions.

The administration is e.g. in form of tablets having a dosage of between 0.5 to 2.5 mg per tablet. Of course, the compound may be administered by other ways, typically, administered systemically by known means.

As used herein, the term "comprising", "comprises", "containing" or "contains" includes the embodiments of "consisting of" or "consist".

In another embodiment of the present invention relates to a composition containing a combination of an inhibitory or cytotoxic agent against plasma cells as defined herein and a B-cell depleting agent or an inhibitor of B-cell activation. Said composition is particularly useful as a pharmaceutical composition, e.g. for use in the treatment of chronic fatigue syndrome.

That is, it is preferred that the pharmaceutical composition is a composition containing a combination of an inhibitory or cytotoxic agent against plasma cells and a B-cell depleting agent or an inhibitor of B-cell activation for use in the treatment of chronic fatigue syndrome wherein the combination is administered simultaneously, separately or sequentially.

In a preferred embodiment, the pharmaceutical composition is designed to allow administration of the inhibitory or cytotoxic agent against plasma cells in a pharmaceutically effective dosage over a time range of the first six weeks of treatment, preferably over a time range of the first eight weeks of treatment, like within three month or four months from the beginning of the treatment. Of course, the treatment regimen depends on the drug administered as well as on the way of administration. The skilled artisan is well aware of suitable dosages and treatment regimen depending on the drug. For example, the same dosages of the inhibitory or cytotoxic drugs may be administered as it is the case for other types of diseases or disorders the same inhibitory or cytotoxic agent against plasma cells are useful.

In addition, the pharmaceutical composition is designed that the B-cell depleting agent or the inhibitor of B-cell activation is adapted for administration 1 or 2 in fusions twice within the first two weeks and, there after, administering the B-cell depleting agent or the inhibitor of B-cell activation once every two, three or four months for maintaining the beneficial effect.

As used herein, the term "B-cell depletion" or "B-cell depleting activity" refers to the ability of the entity, either a chemical or biological entity, e.g. an antibody, to reduce circulating B-cell levels in a subject. B-cell depletion may be achieved e.g. by inducing cell death or reducing proliferation.

As used herein, the term "inhibition of B-cell activation" refers to the ability of the entity, either a chemical or biological entity, to reduce or fully inhibit an activation of B-cells in a subject. The inhibition of B-cell activation can be determined by known means, e.g. by determining marker of B-cell activation.

The "CD20" antigen, or "CD20," is about 35-kDanon-glycosylated phosphoprotein found on the surface of greater than 90% of B cells from peripheral blood or lymphoid organs in humans. CD20 is present on both normal B cells as well as malignant B cells, but is not expressed on stem cells or plasma cells. Other names for CD20 in the literature include "B-lymphocyte-restricted antigen" and "Bp35". The CD20 antigen is described in Clark et al. Proc. Natl. Acad. Sd. (USA) 82:1766 (1985), for example. The term CD20 includes the equivalent molecules of other species than human. Recently, low level expression of CD20 on a subset of T-cells and NK-cells has been reported.

A "B-cell" is a lymphocyte that matures within the bone marrow, and includes a naive B cell, memory B cell, or effector B cell including plasmablasts but not necessarily plasma cells.

In a broader sense, the present invention relates not only to the use of antibodies or fragments thereof for the treatment of CFS, but to the use of antagonists of the CD20 molecule in general having a B-cell depleting activity for the treatment of CFS.

An "antagonist" or "B-cell depleting agent" which is used herein interchangeably is a molecule which, e.g. upon binding to a B cell surface marker, like CD20 on B cells, destroys or depletes B cells in a mammal and/or interferes with one or more B cell functions, e.g. by reducing or preventing a humoral response elicited by the B cell. The antagonist or B-cell depleting agent according to the present invention is able to deplete B cells (i.e. reduce circulating B cell levels) in a mammal treated therewith. Such depletion may be achieved via various mechanisms, such as antibody-dependent cell-mediated cytotoxicity (ADCC) and/or complement dependent cytotoxicity (CDC), inhibition of B cell proliferation and/or induction of B cell death (e.g. via apoptosis). Antagonists included within the scope of the present invention include antibodies, synthetic or native sequence peptides and small molecule antagonists which bind to the B cell surface marker, optionally conjugated with or fused to a cytotoxic agent. A preferred antagonist is a CD20 antibody or CD20-binding antibody fragment. Furthermore, small molecule antagonists are preferred, like the known B-cell depleting agent Methotrexate.

Insofar that other cells than B-cells express the CD20 antigen like a subset of T-cells or NK-cells, these cells are also depleted with the B-cells depleting agent being an agent acting via CD20.

Antagonists which "induce apoptosis" are those which induce programmed cell death, e.g. of a B cell, as determined by standard apoptosis assays, such as binding of annexin V, fragmentation of DNA, cell shrinkage, dilation of endoplasmic reticulum, cell fragmentation, and/or formation of membrane vesicles (called apoptotic bodies).

The term "antibody" herein is used in the broadest sense and specifically covers monoclonal antibodies, polyclonal antibodies, multispecific antibodies {e.g. bispecific antibodies) formed from at least two intact antibodies, as well as chimeric antibodies, e.g. humanised antibodies and antibody fragments so long as they exhibit the desired biological activity.

In a preferred embodiment, the antibody useful for the treatment of CFS is a B-cell depleting CD20-binding antibody fragment.

"CD20-binding antibody fragments" comprise a portion of an intact antibody which comprises the antigen binding region thereof. Examples of antibody fragments include Fab, Fab', F(ab')2, and Fv fragments; diabodies; linear antibodies; single-chain antibody molecules; and multispecific antibodies formed from antibody fragments. For the purposes herein, an "intact antibody" is one comprising heavy and light variable domains as well as an Fc region.

Moreover, it is assumed that other B-cell depleting agents or an inhibitor of B-cell activation, in particular, anti-CD22 antibodies, like Epratuzumab or anti-CD19 humanized antibodies, like MDX-1342, can be used for the treatment of CFS.

The terms "Rituximab" or "RITUXAN®" or "mabthera" herein refer to the genetically engineered chimeric murine/human monoclonal antibody directed against the CD20 antigen and designated "C2B8" in U.S. Pat. No. 5,736,137, expressly incorporated herein by reference, including fragments thereof which retain the ability to bind CD20. Purely for the purposes herein and unless indicated otherwise, "humanized 2H7" refers to a humanized antibody that binds human CD20, or an antigen-binding fragment thereof, wherein the antibody is effective to deplete primate B cells in vivo.

The expression "effective amount" of the B-cell depleting agent or antagonist, in particular of the anti-CD20 antibody or CD20-binding antibody fragment thereof, refers to an amount of the B-cell depleting agent or antagonist which is effective for treating CFS. For example, the anti-CD20 antibody for the treatment of chronic fatigue syndrome/myalgic encephalomyelitis is administered in the range of 10 mg to 5000 mg per dosage. For example, the dosage may be in the range of from 100 to 1000 mg/m$^2$, in particular, 500 mg/m$^2$ as a single infusion for Rituximab. Typically, the dosage for Methotrexate is in the range of 5 mg to 30 mg per week.

In one preferred embodiment, the B-cell depleting agent or an inhibitor of B-cell activation is a chemical entity, e.g. a small molecule. A variety of B-cell depleting agents or an inhibitor of B-cell activation are known in the art for example known B-cell depleting agents are BAFF-antagonists. Furthermore, known B-cell depleting agents include antagonists of BR3, agonists of alpha-4-integrins etc. For example, Methotrexate is an analogue of folic acid displaying B-cell depleting activity. Other useful B-cell depleting agents are small modular immunopharmaceuticals (SMIP) against CD20. For example, SMIP acting as B-cell depleting agents are TRU-015 or SBI-087 of Trubion Pharmaceuticals. Also, SMIP can be single chain polypeptides, smaller than antibodies, having a potent B-cell depletion activity or B-cell inhibitory activity.

In a preferred embodiment, a combination of an anti CD20 antibody and representing a biological entity of a B-cell depleting agent and Methotrexate, representing a chemical entity of a B-cell depleting agent, can be used for treating chronic fatigue syndrome of myalgic encephalomyelitis. Administration of these entities may be effected simultaneously, separately or sequentially. For example, in a first regimen either the antibody or Methotrexate is administered to the subject while in a second regimen the other agent is administered.

The composition comprising the B-cell depleting agent or an inhibitor of B-cell activation, the antagonist, in particular, the anti CD20 antibody or the CD20-binding antibody fragment thereof, will be formulated, dosed, and administered in a fashion consistent with good medical practice. Factors for consideration in this context include the stage of the particular disease or disorder being treated, the particular mammal being treated, the clinical condition of the individual subject, the site of delivery of the agent, the method of administration, the scheduling of administration, and other factors known to medical practitioners. The effective amount of the B-cell depleting agent, like an antibody or antibody fragment to be administered will be governed by such considerations. As a general proposition, the effective amount of the antagonist administered parenterally per dose will be in the range of about 20 mg/m$^2$ to about 10,000 mg/m$^2$ of subject body, by one or more dosages. Exemplary dosage regimens for intact antibodies include 375 mg/m2 weekly×4; 1000 mg×2 (e.g. on days 1 and 15); or 1 gram×3. The antibody for the administration to a subject in a single therapeutically effective dosage of said antibody is of 50 to 2000 mg/m$^2$ or multiple of therapeutically effective dosages of said antibody or CD20-binding antibody fragment thereof of 50 to 2000 mg/m2. As noted above, however, these suggested amounts of antibody are subject to a great deal of therapeutic discretion. The key factor in selecting an appropriate dose and scheduling is the result obtained, as indicated above. The B-cell depleting agent antagonist, like the antibody, is administered by any suitable means, including parenteral, topical, subcutaneous, intraperitoneal, intrapulmonary, intranasal, and/or intralesional administration. Parenteral infusions include intramuscular, intravenous, intraarterial, intraperitoneal, or subcutaneous administration. Intrathecal administration is also contemplated. In addition, the B-cell depleting agent antagonist, like the antibody may suitably be administered by pulse infusion, e.g., with declining doses of the antagonist. Preferably the dosing is given by intravenous injections.

In another embodiment, the combination is a combination of an inhibitory or cytotoxic agent against plasma cells and a B-cell depleting agent or an inhibitor of B-cell activation wherein the said B-cell depleting agent is Methotrexate.

Furthermore, the combination may be in form of at least two different components whereby each component may be separately administered. For example, while one component of the combination according to the present invention may be provided systemically, at least one other component may be adapted for local administration or mucosal administration.

Pharmaceutical Formulations

Therapeutic formulations of the inhibitory or cytotoxic agents against plasma cells and, optionally, the B-cell depleting agents, like antibodies or other antagonists used in accordance with the present invention are prepared for storage by mixing an antibody or a fragment thereof having the desired degree of purity with optional pharmaceutically acceptable carriers, excipients or stabilizers {Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl parabene; catechol; resorcinol; cyclohexanol; 3-pentanol; and m-cresol); low molecular weight (less than about 10 residues) polypeptides; proteins, such as serum albumin, gelatine, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Exemplary anti-CD20 antibody formulations which may form the bases of the compositions according to the present invention are described in WO98/56418, expressly incorporated herein by reference. This publication describes a liquid multidose formulation comprising 40 mg/mL Rituximab, 25 mM acetate, 150 mM trehalose, 0.9% benzyl alcohol, 0.02% polysorbate 20 at pH 5.0 that has a minimum shelf life of two years storage at 2-8° C. Another anti-CD20 formulation of interest comprises 10 mg/mL Rituximab in 9.0 mg/mL sodium chloride, 7.35 mg/mL sodium citrate dihydrate, 0.7 mg/mL polysorbate 80, and Sterile Water for injection, pH 6.5. Lyophilized formulations adapted for subcutaneous administration are described in U.S. Pat. No. 6,267,958 (Andya et ah). Such lyophilized formulations may be reconstituted with a suitable diluent to a high protein concentration and the reconstituted formulation may be administered subcutaneously to the mammal to be treated herein. Crystalized forms of the antibody or antagonist are also contemplated. See, for example, US 2002/0136719A1.

The active ingredients may also be entrapped in microcapsules prepared, for example, by coacervation techniques or by interfacial polymerization, for example, hydroxymethylcellulose or gelatine-microcapsules and poly(methylmethacylate) microcapsules, respectively, in colloidal drug delivery systems (for example, liposomes, albumin microspheres, microemulsions, nanoparticles and nanocapsules)

or in macroemulsions. Such techniques are disclosed in Remington's Pharmaceutical Sciences 16th edition, Osol, A. Ed. (1980). Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly(2-hydroxyethylmethacrylate), or poly(vinyl-alcohol)), polylactides (U.S. Pat. No. 3,773,919), non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydiOxybutyric acid. The formulations to be used for in vivo administration must be sterile. This is readily accomplished by filtration through sterile filtration membranes.

Moreover, the present invention relates to a kit comprising a) a first component which comprises an inhibitory or cytotoxic agent against plasma cells as defined herein, and b) a second component which comprises a B-cell depleting agent or an inhibitor of B-cell activation as defined herein.

It is preferred, that this kit is for use in the treatment of CFS.

It is preferred that the method for treating CFS with the inhibitory or cytotoxic agent against plasma cells comprises the administration of a suboptimal or low dosage at the beginning. In particular, the starting dosage may be reduced to avoid any undesired side effects. Over the time, the dosage may be increased to dosages as administered e.g. in angina pectoris.

Furthermore, the dosage may be an immediate release or sustained dosage depending on the way of administration.

In an embodiment, first the proteasome inhibitor is administered for 2-3 cycles, and thereafter, preferably with a period of time of at least two weeks, like four weeks or two months, the B-cell depleting agent is administered in four courses (1, 2, 3 or 4 courses.

The administration may be systemically or locally via the enteral or parenteral way. For example, topical administration may be affected, e.g. by a patch or pavement for sustained release alternatively, an inhibitory or cytotoxic agent against plasma cells may be administered by way of inhalation or by other mucosal ways.

In a preferred embodiment, the method of treatment comprises administration of the inhibitory or cytotoxic agent against plasma cells in combination with a B-cell depleting agent or an inhibitor of B-cell activation. That is, a combined treatment with an inhibitory or cytotoxic agent against plasma cells and the B-cell depleting agent or an inhibitor of B-cell activation as defined herein is particularly preferred.

Both components may be administered simultaneously, separately or sequentially to said subject suffering from CFS. For example, an inhibitory or cytotoxic agent against plasma cells may be administered by inhalation while the B-cell depleting agent or an inhibitor of B-cell activation is administered by the way of infusion. Furthermore, while an inhibitory or cytotoxic agent against plasma cells may be administered on a daily basis, the B-cell depleting agent or an inhibitor of B-cell activation may be administered initially once a week over two weeks and, thereafter, in a free determined time of schedule, e.g. every second or every third month.

In particular, an inhibitory or cytotoxic agent against plasma cells may be administered during the initial 4 to 12 weeks, like during the first 4 to 8 weeks of treatment, e.g. the initial 4, 5, 6, 7, 8, 9, 10, 11, 12 weeks to allow immediate or rapid relief of the symptoms of CFS while the administration at the B-cell depleting agent or an inhibitor of B-cell activation as defined herein allows relief to the symptoms of the subject suffering from CFS over a long time period due to the delayed effectiveness thereof.

In particular, embodiments of the present invention refer to administration of the inhibitory or cytotoxic agent against plasma cells during the initial 4 to 12 weeks in e.g. 1, 2, 3 or 4 courses. Treatment is continued with a period of time with no administration of an active agent and continued with administration of the B-cell depleting agent, in particular, the anti-CD20 antibody or antibody fragments as defined herein for a period of time including one to one, two, three or four courses of administration, as described above.

EXAMPLES

The invention will be described further by a way of examples. It is understood that the examples illustrate the invention further without limiting the same.

Patient 1:

Patient 1 was a woman aged 37 years, who had ME/CFS for 22 years. She participated in the first double-blind randomized trial using Rituximab versus placebo (two infusions two weeks apart, followed by observation), as described herein. She had no improvement during that study, and after unblinding of the trial she was shown to be allocated to the placebo group. She then later participated in the open-label phase II trial using Rituximab maintenance, as described herein, and the experienced a long-standing and impressive clinical response lasting for more than 3 years before gradual relapse. The patient was then retreated with Rituximab, again with the same pattern and a long-lasting clinical response for more than 3 years before again gradual relapse.

In September 2019 she had a mild-to-moderate ME/CFS severity but with increasing symptoms, and it was decided to offer her the proteasome-inhibitor bortezomib according to the present invention. She received Bortezomib subcutaneously says 1, 4, 11 and 15. In the first course she had 1.0 mg/m$^2$ (i.e. 70% of the dose used in malignant plasma cell disease, multiple myeloma), with no bortezomib-associated side effects except an exanthema around the injection site, with some erythema and itching at the skin on the abdominal wall. She received the second course at approximately four weeks, with Bortezomib 1.3 mg/m$^2$ subcutaneously (100% dose) at days 1, 4, 8 and 11, with increasing local reaction at the injection site and with some transient fatigue and pain in the muscles as possible side effects. She therefore received the third course of Bortezomib as an intravenous infusion with the same dose 1.3 mg/m$^2$, given at days 1, 4, 8 and 11. After the third intravenous course she had a transient exanthema along the vein on the arm in which she had received the infusion, interpreted as an allergic reaction and we decided to stop further Bortezomib treatment.

However, at week 10 from start of bortezomib treatment, she experienced gradual improvement of all her ME/CFS symptoms, such as postexertional malaise (PEM), pain especially in muscles and joints, cognitive disturbances and sleep problems. She had increasing energy, increased exertion and was able to perform many new tasks. Knowing the disease from many years of experience, she was certain that the intervention had a positive effect on the ME/CFS symptoms. The self-reported symptom improvement was supported by measured steps per 24 hours (Fitbit armband) and in the response period we registered more than 10.000 steps per day.

The effect lasted for approximately 7 weeks before she started experiencing gradual relapse of the ME/CFS symptoms. Therefore, she has received Rituximab infusions 4 months apart, and is in stable and impressive clinical response now.

Patient 2:

Patient 2 was a woman aged 46 years, who had ME/CFS of moderate-to-severe disease severity, i.e. she was housebound and in periods more or less bedridden. She had previously participated in the open-label trial assessing cyclophosphamide intravenous infusions in ME/CFS mentioned herein, and experienced a clinical response lasting for almost a year before gradual relapse. She received the first course of Bortezomib subcutaneously at 1.0 mg/m² days 1, 4, 8 and 11, with a minimal skin reaction at the injection site and no other side effects. She received the second and third courses at 1.3 mg/m² approximately 4 weeks apart.

From 7 weeks after start of Bortezomib intervention, she experienced a gradual and consistent improvement of all her ME/CS symptoms, with increasing energy, less pain, less PEM, less dizziness and improved cognitive function. Her Fitbit armband verified her description of improvement, with increasing steps per 24 hours from mean 1500-2000 before intervention to approximately 4000, up to 7000 on single days, after response. She received in total 6 courses of Bortezomib, but after the last course she noted discomfort in her lower extremities at the legs and feet, and some constipation. She had a lasting response until 6 weeks after the last Bortezomib infusion, in total 16 weeks, before gradual relapse. Therefore, she then received Rituximab infusions 4 months apart, and has now again an increasing degree of clinical response approximately 4 months after start of Rituximab infusions.

The invention claimed is:

1. A method for the treatment of myalgic encephalomyelitis (ME)/chronic fatigue syndrome (CFS) comprising administering to a subject in need thereof a therapeutically effective amount of a cytotoxic agent against plasma cells to reduce antibody production, wherein the cytotoxic agent is an antibody directed against CD38 and wherein the antibody directed against CD38 is Daratumumab.

2. The method according to claim 1 wherein said cytotoxic agent is adapted for systemic administration.

3. The method according to claim 1 wherein said cytotoxic agent is administered in a pharmaceutically effective dosage systemically.

* * * * *